United States Patent [19]

Smith et al.

[11] Patent Number: 4,833,258

[45] Date of Patent: May 23, 1989

[54] INTERMEDIATES USEFUL IN THE PREPARATION OF HMG-COA REDUCTASE INHIBITORS

[75] Inventors: Robert L. Smith; Ta Jyh Lee, both of Lansdale, Pa.

[73] Assignee: Merck & Co., Inc., Rahway, N.J.

[21] Appl. No.: 15,637

[22] Filed: Feb. 17, 1987

[51] Int. Cl.$^4$ .......................................... C07D 309/30
[52] U.S. Cl. .................... 549/292; 549/347; 549/373; 549/374; 549/451; 549/453; 568/583; 568/591; 558/428
[58] Field of Search ............... 549/292, 347, 373, 374, 549/451, 453; 568/583, 591

[56] References Cited

U.S. PATENT DOCUMENTS

| | | | |
|---|---|---|---|
| 4,376,863 | 3/1983 | Lam | 549/292 |
| 4,448,979 | 5/1984 | Terahara et al. | 549/292 |
| 4,517,373 | 5/1985 | Terahara et al. | 549/292 |
| 4,537,859 | 8/1985 | Terahara et al. | 435/146 |

FOREIGN PATENT DOCUMENTS

J59-122483-A 7/1984 Japan.

OTHER PUBLICATIONS

Hesse, Adv. Free Radical Chem., 3, 83–137 (1969).
Barton, Pure Appl. Chem., 16, 1–15 (1968).
Akhtar, Adv. Photochem., 2, 263–304 (1964).

*Primary Examiner*—Richard L. Raymond
*Assistant Examiner*—A. A. Owens
*Attorney, Agent, or Firm*—Melvin Winokur; Joseph F. DiPrima

[57] ABSTRACT

Novel intermediates and a novel process for their preparation, where said intermediates are useful in the preparation of 6-hydroxymethyl and related oxidation derivatives of mevinolin and analogs thereof, are disclosed.

10 Claims, No Drawings

INTERMEDIATES USEFUL IN THE PREPARATION OF HMG-COA REDUCTASE INHIBITORS

BACKGROUND OF THE INVENTION

Hypercholesterolemia is known to be one of the prime risk factors for ischemic cardiovascular disease, such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof.

The naturally occuring compounds and their semi-synthetic analogs have the following general structural formulae:

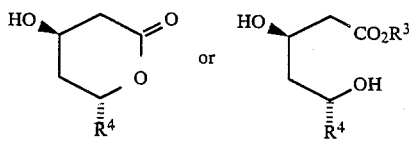

wherein:

$R^3$ is hydrogen, $C_{1-5}$ alkyl or $C_{1-5}$ alkyl substituted with a member of the group consisting phenyl, dimethylamino, or acetylamino; and $R^4$ is:

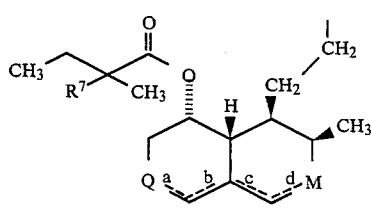

wherein Q is

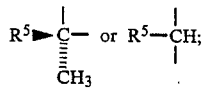

$R^5$ is H or OH; M is

$R^6$ is hydrogen or hydroxy;

$R^7$ is hydrogen or methyl; and a, b, c, and d represent single bonds, one of a, b, c or d represents a double bond, or both a and c or both b and d represent double bonds provided that when a is a double bond, Q is

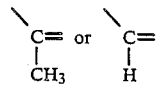

and when d is a double bond, M is

U.S. Pat. No. 4,517,373 discloses semi-synthetic hydroxy containing compounds represented by the above general formula wherein $R^4$ is

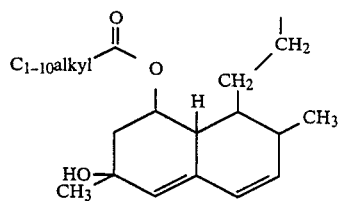

and

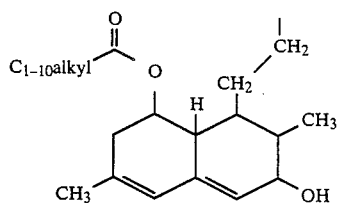

U.S. Pat. Nos. 4,537,859 and 4,448,979 also disclose semi-synthetic hydroxy-containing compounds represented by the above general formula wherein $R^4$ is

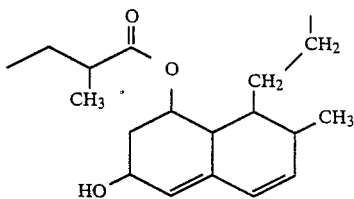

and

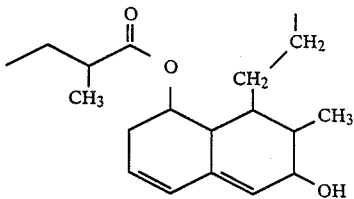

These compounds are prepared by the action of certain microorganisms on the corresponding non-hydroxylated sybstrates. One such organism described in U.S. Pat. No. 4,537,859 is of the genus Nocardia.

U.S. Pat. No. 4,376,863 discloses a fermentation product, isolated after cultivation of a microorganism belonging to the genus Aspergillus, which has a hydroxy containing butyryloxy side chain and is represented by the above general formula wherein $R^4$ is

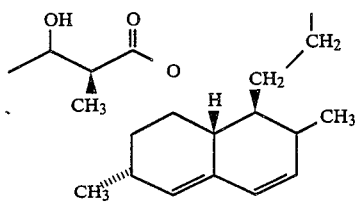

Japanese unexamined patent application No. J59-122,483-A discloses a semi-synthetic hydroxy-containing compound respresented by the above general formula wherein $R^4$ is

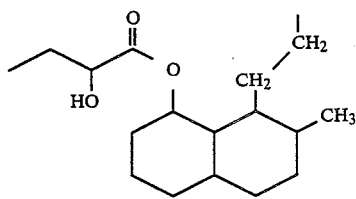

U.S. patent application Ser No. 877,041 filed June 23, 1986 discloses 6-substituted compounds of the above gneral formula wherein $R^4$ is

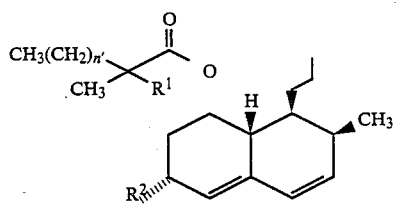

wherein
n' is 1 to 5
$R^1$ is hydrogen or $C_{1-5}$ alkyl
$R^2$ is $CH_2OH$ or $CO_2R$ The compounds of U. S. patent application Ser. No. 877,041 were prepared by a microbiological conversion of mevinolin or an analog thereof with a 6-methyl substituent.

The literature discloses a reaction known as the Barton Reaction by which a hydrogen in the δ position to an OH group can be abstracted to afford a carbon radical which can be oxidized. (See Hesse Adv. Free-Radical Chem. 3, 83–137 (1969); Barton, Pure Appl. Chem. 16, 1–15 (1968); Arthar, Adv. Photochem. 2, 263–304 (1964).

DETAILED DESCRIPTION OF INVENTION

This invention relates to novel intermediates, and a novel process for their preparation, where said intermediates are useful in the preparation of 6-desmethyl-6-hydroxy methyl (A) and related oxidation derivatives (B) of mevinolin and analogs thereof at the 8-acyl side chain and unsaturation within the polyhydronapthyl ring. Said 6-hydroxymethyl and related oxidation derivatives of mevinolin and analogs thereof are useful in treating hypercholesterolemia and are disclosed in copending patent application, Ser. No. 001,933, filed Jan. 9, 1987.

The intermediates of the instant invention are prepared and used to form the 6-desmethyl-6-hydroxymethyl mevinolin analogs (A) in a process which comprises (A) reacting the compound (1)

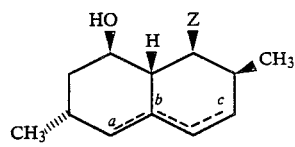

wherein a, b and c represent single bonds or one of a, b, or c represents a double bond; and wherein Z is selected from a group consisting of
(a)

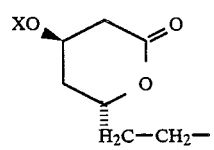

wherein X is trialkylsilyl, alkyldiphenylsilyl, or tetrahydropyranyl, or a like hydroxyl protecting group;
(b) $CH_2CH_2CN$
(c)

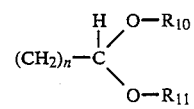

wherein n is 0 or 2 and $R_{10}$ and $R_{11}$ are independently lower alkyl or $R_{10}$ and $R_{11}$ together with the oxygens to which they are attached and the carbon bonded to the oxygens form a ring of 5 to 10 atoms; with nitrosyl chloride in the presence of a base to yield the compound (2)

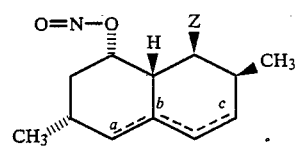

(B) irradiating the compound (2) with light to obtain compound (3)

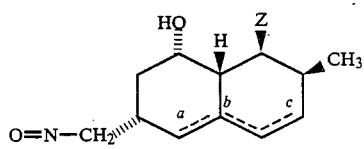

(C) heating or treating the compound (3) with organic bases in protic solvent to afford compound (4)

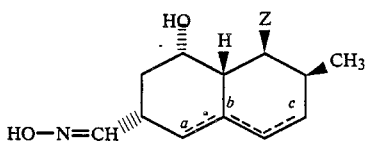

(4)

(D) treating compound (4) with an alkali metal nitrite or aqueous formaldehyde solution in the presence of an acid catalyst to yield an equilabrium mixture of compound (5) and compound (6)

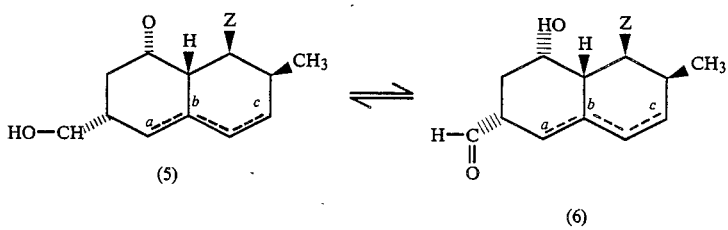

(E) treating the mixture of compound (5) and compound (6) with a reducing agent to obtain compound (7)

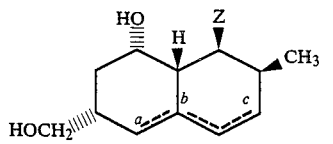

(7)

(F) reacting compound (7) with an alkyldiarylsilyl halide, tralkylsilyl halide, or tetrahydropyran or other reagents useful for protecting a hydroxy group, to afford compound (8)

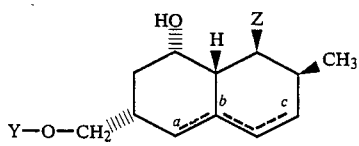

(8)

where Y=alkyldiarylsilyl, trialkylsilyl, tetrahydropyranyl, or a like hydroxyl protecting group (G) acylating compound (8) with an appropriate alkanoyl halide or alkanoic acid and hydrolyzing hydroxyl protecting groups to yield the compounds of the formula (9)

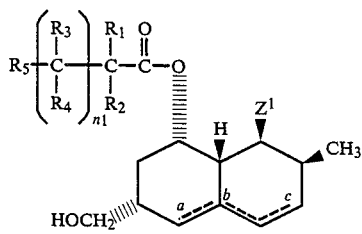

(9)

wherein:

$n_1$ is 0 to 5

$R_1$ and $R_2$ independently are hydrogen, $C_{1-5}$ alkyl, or $R_1$ and $R_2$ together with the carbon atom to which they are attached form a carbocyclic ring of 3 to 8 carbon atoms;

$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when $n_1$ is 2 to 5, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;

$R_5$ is hydrogen, halogen, hydroxy, $C_{1-5}$ alkyl, phenyl or substituted phenyl in which the substituents are V and W, or $R_5$ is a group selected from:

(a) $C_{1-5}$ alkylthio or phenylthio or substituted phenylthio in which the substituents are V and W, (b) $C_{1-5}$-alkanoyloxy-$C_{1-4}$-alkyl, (c)

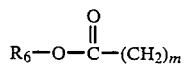

in which m is 0 to 3 and $R_6$ is $C_{1-5}$ alkyl;

(d)

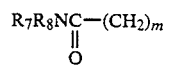

in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperazinyl or thiomorpholinyl;

(e)

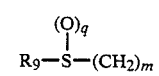

'in which q is 0 to 2 and $R_9$ is $C_{1-5}$ alkyl or phenyl or substituted phenyl in which the substituents are V and W;

V and W independently are hydrogen, halogen, hydroxy, trifluoromethyl, $C_{1-3}$ alkyl, $C_{1-3}$ alkyloxy and hydroxy-$C_{1-3}$ alkyl;

Z' is selected from a group consisting of:

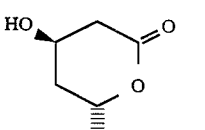 a.

 b.

-continued c.
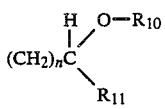

One embodiment of this invention is the class of compounds of formula (3),

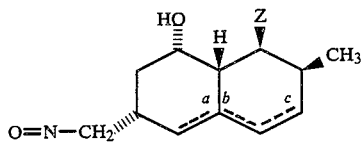

and a process for making said compounds. In a subclass of this embodiment are the compounds of formula (3) wherein Z is

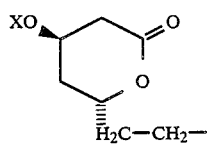

and a, b and c all represent single bonds. Exemplifying this subclass is:
(1) 6(R)-[2-[8(S)-hydroxy-2(S)-methyl-6(S)-nitrosylmethyl-1,2,3,4,4a(S),5,6,7,8,8a(S)-decahydronaphthyl-1(S)]ethyl]-4(R)-tertbutyldimethylsilyloxy)-3,4,5,6-tetrahydro-2H-pyran-2-one.

A further illustration of this embodiment is the subclass of compounds and process for making said compounds wherein Z is

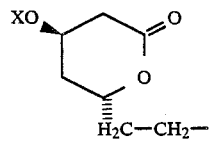

and one of a, b, or c is a double bond. Exemplifying this subclass is:
(1) 6(R)-[2-[8(S)-hydroxy-2(S)-methyl-6(R)-nitrosylmethyl-1,2,3,4,6,7,8,8a(R)-octahydronaphthyl-1(S)]ethyl]-4(R)-(tertbutyldimethylsilyloxy)-3,4,5,6-tetrahydro-2H-pyran-2-one.

A second embodiment of this invention is the class of compounds of formula (7),

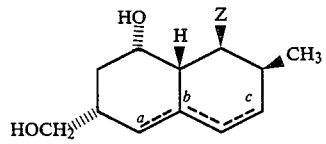

and a process for making said compounds. In a subclass of this embodiment are the compounds of formula (7) wherein Z is

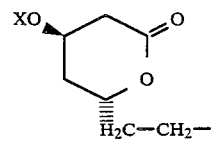

and a, b, c all represent single bonds. Exemplifying this subclass is:
(1) 6(R)-[2-[8(S)-hydroxy-2(S)-methyl-6(S)-hydroxymethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one.

A further illustration of this embodiment is the subclass of compounds and process for making said compounds wherein Z is

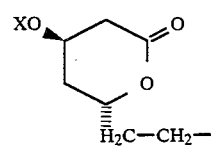

and one of a, b, or c represents a double bond. Exemplifying this subclass is:
(1) 6(R)-[2-[8(S)-hydroxy-2(S)-methyl-6(R)-hydroxymethyl-1,2,3,4,6,7,8,8a(R)-octahydronaphthyl-1(S)]ethyl]-4(R)-(tert-butyldimethylsilyloxy)-3,4,5,6-tetrahydro-2H-pyran-2-one.

A third embodiment of this invention is the preparation of the class of compounds of formula (9).

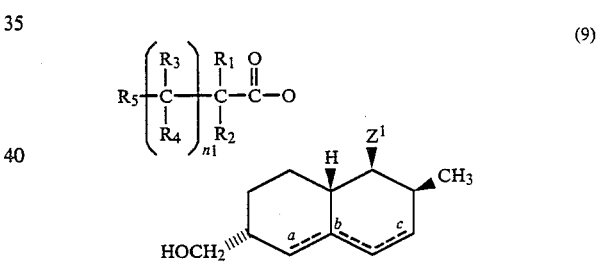

In one class of this embodiment $n_1$ is 0 to 3, $R_1$ is methyl, $R_2$ is hydrogen or methyl. In one subclass are the compounds wherein Z' is:

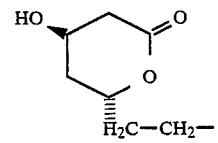

and a, b, and c all represent single bonds. Exemplifying this subclass is:
6(R)-[2-[8(S)-(2,2-dimethylbutyryloxy)-6(S)-hydroxymethyl-2(S)-methyl-1,2,3,4,4a(S),5,6,7,8,8a(S)-decahydronaphthyl-1(S)]ethyl]-(R)-hydroxy-3,4,5,6-tetrahydro-2H-pyran-2-one. In another subclass of this embodiment one of a, b, or c represents a double bond. Exemplifying this subclass is:
6(R)-[2-[8(S)-(2,2-dimethylbutyryloxy)-6 (R)-hydroxymethyl-2(S)-methyl-1,2,3,4,6,7,8,8a(R)-octahydronaphthyl-1(S)]ethyl]-4(R)-hydroxy-3,4,5,6-tetrahydro-2H-pyran-2-one.

In another class of this embodiment $R_1$ and $R_2$ together with the carbon to which they are attached form a carbocyclic ring of 3 to 8 carbons. In one subclass are the compounds wherein Z' is

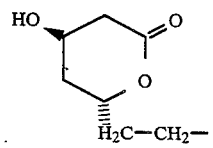

and a, b, and c all represent single bonds. Exemplifying this subclass is:
6(R)-[2-[8(S)-(cyclohexylcarbonyloxy)-6(S)-hydroxymethyl-2(S)-methyl-1,2,3,4,4a(S),5,6,7,8,a(S)-decahydronaphthyl-1(S)]-ethyl]-4(R)-hydroxy-3,4,5,6-tetrahydro-2H-pyran-2-one.

In another subclass are the compounds wherein Z is:

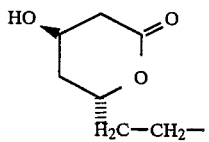

and one of a, b, or c represents a double bond. Exemplifying this subclass is:
6(R)-[2-[8(S)-(cyclohexylcarbonyloxy-6(R)-hydroxymethyl-2(S)-methyl-1,2,3,4,6,7,8,8a(R)-octahydronaphthyl-1(S)]-ethyl]-4(R)-hydroxy-3,4,5,6-tetrahydro-2H-pyran-2-one.

The reaction of a compound of formula (1) with nitrosyl chloride is conducted at a temperature between −10° and 10 ° C., preferably at 0° C. for a period of from 10 minutes to 2 hours, most preferably 0.5 hour at 0° C., in the presence of a basic solvent. Illustrative of such basic solvents are pyridine and quinoline and the like. A sufficient amount of nitrosyl chloride is used such that a saturated solution of nitrosyl chloride is formed, and the reaction proceeds to completion.

The irradiation of a compound of formula (2) is conducted using light of wavelength greater than 320 Å. One source of the irradiation is a medium pressure mercury lamp at a temperature between 0° and 30° C., preferably at 20° C., for a period of from 0.5 to 5 hours, most preferably 1 hour at 20° C., in an inert solvent. Examples of such inert solvents are hydrocarbons such as benzene, hexanes and the like.

The rearrangement of a compound of formula (3) is conducted at a temperature between 60° and 100° C., preferably at 80° C. for a period of 0.5 to 10 hours, most preferably for 2 hours at about 80° C., in the presence of a protic solvent. Illustrative of such protic solvents are alcohols such as isopropanol or 2-butanol and the like.

The reaction of a compound of formula (4) with an alkali metal nitrite is conducted at a temperature between −10° and 25° C., preferably at 10° C., for a period of from 0.5 to 5 hours, most preferably 2 hours at 10° C. in the presence of aqueous acid. The alkali metal nitrites which may be used are sodium nitrite, lithium nitrite and the like. The acids which may be utilized in this reaction include organic acids, such as acetic, propionic acid and the like and inorganic acids, such as sulfuric acid and the like. The amount of compound (4) to alkali metal nitrite can vary between 1.0 equivalents of (4) to 15 equivalents of alkali metal nitrite. However, a ratio of 1.0 to 10.0 is preferred.

The reaction of the mixture of compounds of formulae (5) and (6) with a reducing agent is conducted at a temperature between −10° and 10° C., preferably at 0° C., for a period of 15 minutes to 2 hours, most preferably 0.5 hour at 0° C., in an inert solvent. The reducing agents which may be utilized are sodium borohydride, diborane and the like. The reaction may be carried out in such inert solvents as aqueous ethanol, aqueous tetrahydrofuran and the like.

The reaction of a compound of formula (7) with tert-butyldiphenylsilyl halide or tert-butyldimethylsilyl halide to protect the 6-hydroxymethyl moiety is carried out following the procedures disclosed in U.S. Pat. No. 4,444,784. The 6-hydroxymethyl group is protected using tetrahydropyran according to the procedures described in the text "Protective Groups in Organic Synthesis" T. W. Greene, 1981, John Wiley & Sons.

A compound of formula (8) is acylated with an alkanoyl chloride, in the presence of lithium bromide and dimethylaminopyridine in pyridine.

Alternatively, the acylation of a compound of formula (8) is conducted with an alkanoyl chloride under standard reaction conditions. This standard acylation procedure is used whenever the alkanoyl chloride is nonhindered at the acyl site, e.g., cyclohexylcarbonyl chloride.

Where the hydroxyl protecting group is trialkysilyloxy or diarylalkylsilyloxy, desilylation is accomplished with tetrabutylammonium fluoride buffered with acetic acid. The tetrahydropyranyl group may be hydrolyzed using standard chemical procedures such as heating with dilute acid.

The starting compound (1) wherein Z is

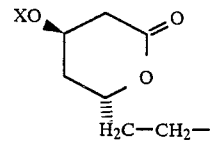

and a, b and c are all single bonds or a or b is a double bond and X is tert-butyldimethylsilyl was prepared by hydrogenating mevinolin according to hydrogenation procedures disclosed in U.S. Pat. No. 4,351,844 followed by hydrolysis of the 8-acyloxy moiety under the conditions disclosed in U.S. Pat. No. 4,444,784 and protection of the 4-hydroxy function in the lactone moiety with a tert-butyldimethylsilyloxy group according to the procedure disclosed in U.S. Pat. No. 4,444,784. Where X is tetrahydropyranyl, the 4-hydroxy function in the lactone moiety is protected according to the procedures described in the text "Protective Groups in Organic Synthesis", T. W. Greene, 1981, John Wiley & Sons.

Alternatively the starting compound (1) wherein Z is

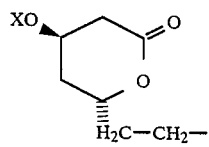

a is a double bond and X is tert-butyldimethylsilyl was prepared from 6(R)-[2-[8(S)-hydroxy-2(S),6(S)-dimethyl-1,2,6,7,8,8a(R)-hexahydro-naphthyl-1(S)]ethyl]-4(R)-(tert-butyl-dimethylsilyloxy)-3,4,5,6-tetrahydro-2H-pyran-2-one by hydrogenation using Wilkinson's catalyst. This hexahydro derivative was readily prepared from mevinolin using standard procedures discussed above.

Starting compounds containing the lactone ring and a double bond in the c position are prepared from the 4a,5-dihydromevinolin derivative disclosed by Albers-Schönberg et al. in J. Antibiot., 34, 507 (1981).

The starting compound (1) where Z is CH₂CH₂CN and a, b, c are all single bonds or a or b is a double bond is prepared from the corresponding aldehyde employing standard chemical transformations. The aldehyde may be prepared using the synthetic methods described by Funk and Zeller (W. E. Zeller Ph.D. Thesis, University of Nebraska, 1985) followed by hydrogenation procedures and hydrolysis as described above. Alternatively the aldehyde may be prepared following the procedure of Deutsch and Snider, Tetrahedron Lett., 24, 3701 (1983) followed by hydrogenation and hydrolysis. Where c is a double bond the aldehyde is prepared following the scheme of Hecker and Heathcock disclosed in J. Am. Chem. Soc., 108,4586 (1986), followed by standard chemical transformations, and hydrogenation and hydrolysis as described above.

The starting compound (1) where Z is

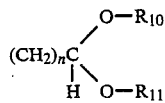

is prepared from the corresponding aldehyde employing standard chemical transformations. The aldehydes are prepared following the procedures described above.

The appropriately substituted acyl chlorides necessary for step (G) are commercially available or prepared from known starting materials.

The compounds of formula (9) wherein Z' is CH₂CH₂CN can be converted into the 6-desmethyl-6-hydroxylmethyl mevinolin analogs (A) by following the procedures detailed in patent application Ser. No. 741,069, filed June 4, 1985.

The compounds of formula (9) wherein Z' is

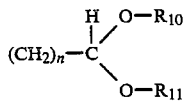

and n=2, can be converted into the 6-desmethyl-6-hydroxymethyl mevinolin analogs (A) by hydrolyzing the aldehyde protecting group and following the procedures detailed in U.S. Pat. No. 4,611,081; where n=0 the lactone ring can be constructed following the procedure outlined by Heathcock, et. al. J. Org. Chem. 49, 3657 (1984).

The following Examples illustrate the present invention and as such are not to be considered as limiting the invention set forth in the claims appended hereto.

EXAMPLE 1

Preparation of 6(R)-[2-[8(S)-(2,2-dimethylbutyryloxy)-2(S)-methyl-6(S)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one.

(a) 6(R)-[2-[8(S)-nitrosyloxy-2(S),6(S)-dimethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (1a)

A stream of nitrosyl chloride gas was passed into a stirred solution of 6(R)-[2-[8(S)-hydroxy-2(S),6(S)-dimethyl-1,2,3,4,4a(S),5,6,7,8,8a(S)-decahydronaphthyl-1(S)]-ethyl]-4(R)-(tert-butyldimethylsilyloxy)-3,4,5,6-tetrahydro-2H-pyran-2-one, (800 mg, 1.82 mmol) in pyridine (14 ml) at 0° C. until the solution was saturated (brownish fumes filled the reaction flask). The resulting mixture was stirred at 0° C. for another 10 minutes, poured into cold water and extracted with diethyl ether. The extract was washed successively with dilute HCl, water and 5% NaHCO₃, dried (MgSO₄), filtered and concentrated to afford the title compound as a white solid: (M.P. 92°–4° C.) nmr (CDCl₃) δ 0.86 (3H, d, J=7 Hz), 0.89 (9H, s), 0.99 (3H, d, J=7 Hz), 2.55 (H, m of d, J=18 Hz), 2.60 (H, d of d, J=18,4 Hz), 4.28 (H, m), 4.53 (H, m), 5.84 (H, m).

Anal Calc'd for C₂₅H₄₅NO₅Si C: 64.20; H: 9.70; N: 3.00. Found: C: 64.09; H: 10.00; N: 3.06.

(b) 6(R)-[2-[8(S)-Hydroxy-2(S)-methyl-6(S)-nitrosylmethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one(1b)

Nitrogen gas was passed through a solution of compound (1a) (870 mg, 1.82 mmol) in benzene (320 ml) for 25 minutes. This solution was irradiated under N₂ with a 450 watt Hanovia medium pressure mercury lamp (pyrex filter) for 40 minutes at room temperature. The reaction mixture was then concentrated in vacuo and the residue applied to a silica gel column. Elution of the column with methylene chloride:acetone=50:1 (V:V) followed by elution of the column with methylene chloride: acetone:2-propanol=100:10:2 (V:V:V) yielded the desired product (1b) as a foamy oil: nmr (CDCl₃) δ 0.83 (3H, d, J=7 Hz), 0.88 (9H, s) 4.10 (H, bs), 4,29 (H, m), 4.64 (2H, d, J=8 Hz), 4.67 (H, m).

(c) 6(R)-[2-[8(S)-Hydroxy-2(S)-methyl-6(S)-hydroxyiminomethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one.(1c)

The compound (1b) (288 mg, 0.616 mmol) was dissolved in isopropanol (15 ml) and heated at reflux for 2.0 hours. After cooling the reaction mixture was concentrated in vacuo to leave a residue which was concentrated to yield the title compound as a gummy oil: nmr (CDCl₃) δ 0.86 (3H, d, J=7 Hz), 0.90 (9H, s) 2.33 (H, d, J=14 Hz), 2.78 (H, m), 4.11 (H, m), 4,32 (H, m), 4.66 (H, m), 7,50 (H, d, J=6 Hz).

(d)
6(R)-[2-[8-Hydroxy-2(S)-methyl-6(S)-formyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one(1d).

Sodium nitrite (477 mg 6.83 mmol) was added at 0° C. in one portion to a stirred solution of compound (1c) (324 mg 0.683 mmol) in acetic acid (14 ml) and water (7ml). The resulting mixture was stirred at 0° C. for 10 minutes, warmed to room temperature and stirred for 2.5 hours. The mixture was then diluted with water and extracted with diethyl ether. This ethereal extract was washed with water, 5% NaHCO$_3$ (twice), dried and filtered. Evaporation of the filtrate in vacuo afforded a brownish oily residue whose nmr is consistent with the structure for Compound (1d). nmr (CDCl$_3$) δ 0.80 (3H, d, J=7 Hz), 0.88 (9H, s), 4,30 (H, m) 4.55 (2H, m)

(e)
6(R)-[2-[8(S)-Hydroxy-2(S)-methyl-6(S)-hydroxymethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one. (1e)

Powdered sodium borohydride (40 mg, 1.05 mmol) was added at 0° C. to a stirred solution of Compound (1d) (296 mg, 0.651 mmol) in 95% ethanol (15 ml) in one portion. The resulting mixture was stirred at 0° C. for 0.5 h, then slowly treated with a solution of aq. (NH$_4$) (0.7 g in 15 ml H$_2$O). The resulting mixture was stirred at 0° C. for 0.5 h, diluted with water (60 ml) and extracted with diethyl ether. This extract was washed with water 5% NaHCO$_3$, dried, filtered and evaporated to give a crude sample which was purified by flash chromatography. Elution of the column with methylene chloride:acetone:2-propanol=100:10:2 (V:V:V) afforded the desired product (1e) as a white solid: mp 124°–7° C.; nmr (CDCl$_3$) δ 0.83 (3H, d, J=7 Hz), 0.90 (9H s), 3.73 (H, d of d, J=11,6 Hz), 3.79 (H, d of d, J=11, 6 Hz), 4.10 (H, bs) 4.31 (H, m), 4.70 (H, m).

Anal Calc'd for C$_{25}$H$_{46}$O$_5$ Si C: 66.03; H: 10.20. Found C: 66.07; H: 10.38.

(f)
6(R)-[2-[8(S)-Hydroxy-2(S)-methyl-6(S)-(tert-butyldiphenylsilyloxymethyl)-1,2,3,4,4a(S),5,6,7,8,8a(S)-decahydronaphthyl-4(R)-(tert-butyldimethylsilyloxy)-3,4,5,6-tetrahydro-2H-pyran-2-one. (1f)

A solution of tert-butyldiphenylsilyl chloride (140 mg, 0.50 mmol) in dimethylformamide (1 ml) was added at 0° C. to a stirred solution of compound (1e) (0.150 g, 0.33 mmol) and imidazole (115 mg, 1.7 mmol) in dimethylformamide (4 ml). The resulting mixture was stirred at 0° C. for 15 minutes. then warmed to room temperature and stirred for 15 hours. The mixture was poured into cold water and extracted with diethyl ether. This ethereal extract was washed with dilute HCl and 5% NaHCO$_3$, dried, filtered and evaporated to leave crude product (1f) which was purified by flash chromatography on a silica gel column. Elution of the column with methylene chloride:acetone=50:1 (V:V) gave the desired product (1f) as a gummy oil: nmr (CDCl$_3$ δ 0.84 (3H, d, J=7 Hz) 0.90 (9H, s), 1.09 (9H, s), 2.99 (H, d, J=6 Hz), 3.7–3.85 (2H, m) 4.02 (H, m), 4.30 (H,m) 4.67 (H, m) 7,3–7.5 (6H, m), 7.65–7.8 (4H, m).

(g)
6(R)-[2-[8(S)-(2,2-Dimethylbutyryloxy)-2(S)-methyl-6(S)-(tert-butyldiphenylsilyloxymethyl)-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one. (1g)

Lithium bromide powder (0.200 g, 2.30 mmol) was added at room temperature under nitrogen in one portion to a stirred solution of 2,2-dimethylbutyryl chloride (0.150 g, 1.11 mmol) in pyridine (3.5 ml). The resulting mixture was stirred at room temperature until it became a homogenous solution (0.5 h) 4,4-Dimethylaminopyridine (DMAP) was then added (80 mg, 0.65 mmol) and a solution of Compound (1f) (229 mg, 0.33 mmol) in pyridine (2.5 ml). The resulting mixture was heated at 90°–95° under N$_2$ for 70 hours. The reaction mixture was cooled, poured into cold water and extracted with diethyl ether. This ethereal extract was washed successively with dilute HCl, water and 5% NaHCO$_3$, then dried, filtered and concentrated in vacuo to afford an oily residue which was purified by flash chromatography on silica gel, eluting with methylene chloride:acetone=200:1 (V:V). The product fractions were further purified by preparative TLC (Analtech SiO$_2$ plates, eluant CH acetone=75:1 (V/V)) to give compound (1g) as a colorless viscous oil. nmr (CDCl$_3$) δ 0.66 (3H, t, J=7 Hz), 0.84 (3H, d, J=7 Hz), 0.9 (9H, s), 0.91 (6H, s), 1.10 (9H, s) 3.51 (H, d of d, J=11.4 Hz) 3.85 (H, t, J=11 Hz), 4.30 (H, m), 4.55 (H, m) 5.08 (H, m) 7.3–7.5(6H, m) 7.6–7.8 (4H, m).

(h)
6(R)-[2-[8(S)-(2,2-Dimethylbutyryloxy)-2(S)-methyl-6(S)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one. (1h)

1 ml of a 1M n-tetrabutylammonium fluoride solution (1 mmol) was added to a stirred mixture of compound (1g) (55 mg, 0.0695 mmol) and acetic acid (0.12 ml, 2.10 mmol) in THF (1.2 ml). The resulting mixture was stirred at room temperature for 36 hours The reaction mixture was heated at reflux for 4.5 hours, cooled to room temperature and poured into cold water and extracted with diethyl ether. The ethereal extract was washed with 5% NaHCO$_3$, dried, filtered, and concentrated in vacuo to yield a residue which was purified by flash chromatography on silica gel. Elution of the column with methylene chloride: acetone=10:1 (V:V) removed the impurities. Further elution with methylene chloride:acetone:2propanol=100:10:5 (V:V:V) afforded compound 1h as a gummy oil: nmr (CDCl$_3$) δ 0.85 (3H, d, J=7 Hz), 0.87 (3H, t, J=7 Hz) 1.16 (3H, s), 1.17 (3H, s), 2.62 (H, m of d, J=18 Hz), 2.73 (H, d of d, J=18, 5 HZ), 3.0 (H, bs), 3.57 (H, d of d, J=11, 6 Hz), 3.80 (H, t, J=11 Hz) 4.34 (H, m), 4.60 (H, m) 5.20 (H, m).

Anal Calc'd for C$_{25}$H$_{42}$O C: 68.46; H: 9.65. Found C: 68.35; H: 9.85.

EXAMPLE 2

Preparation of 6(R)-[2-[8(S)-(Cyclohexylcarbonyloxy)-6(S)-hydroxymethyl-2(S)-methyl-1,2,3,4,4a(S),5,6,7,8,8a(S)-decahydronaphthyl-1(S)]ethyl]-4(R)-hydroxy-3,4,5,6-tetrahydro-2H-pyran-2-one Steps (a)–(f) are identical to those of Example 1.

(g)
6(R)-[2-[8(S)-(Cyclohexylcarbonyloxy)-6(S)-(tert-butyldiphenylsilyloxymethyl)-2(S)-methyl-1,2,3,4,4a(S),5,6,7,8 8a(S)-decahydronaphthyl-1(S)]ethyl]-4(R)-(tert-butyl-dimethylsilyloxy)-3,4,5,6-tetrahydro-2H-pyran-2-one (2g)

A solution of cyclohexylcarbonyl chloride (73 mg, 0.5 mmol) in pyridine (2 ml) was added to a stirred mixture of 6(R)-[2-[8(S)-hydroxy-2(S)-methyl-6(S)-(tert-butyldiphenylsilyloxymethyl)-1,2,3,4,4a(S),5,6,7,8-,8a(S)-decahydronaphthyl-1(S)]ethyl]-4(R)-(tert-butyl-dimethylsilyloxy)-3,4,5,6-tetrahydro-2H-pyran-2-one (Compound 1f) (116 mg, 0.167 mmol) and 4,4-dimethylaminopyridine (24 mg, 0.2 mmol) in pyridine (2 ml). The resulting mixture was stirred at room temperature under nitrogen for 3 hours then heated at 65° C. for 1.5 hours. After cooling, the reaction mixture was poured into cold water and extracted with diethyl ether. The ethereal extract was washed successively with diluted hydrochloric acid, water and 5% NaHCO3. After drying, it was filtered and evaporated in vacuo to leave a residue which was purified by flash chromatography. Elution of the column with methylene chloride:acetone=100:1 (V:V) yielded the desired product 2g as a colorless gummy oil: nmr (CDCl3) δ 0.83 (3H, d, J=7 Hz), 0.90 (9H, s), 1.08 (9H, s), 3.54 (H, d of d, J=11, 6 Hz), 3.83 (H, t, J=11 Hz), 4.28 (H, m), 4.56 (H, m), 5.04 (H, m), 7.32–7.5 (6H, m), 7.6–7.8 (4H, m).

(h)
6(R)-[2-[8(S)-(Cyclohexylcarbonyloxy)-6(S)-hydroxymethyl-2(S)-methyl-1,2,3,4,4a(S),5,6,7,8,8a(S)-decahydronaphthyl-1(S)]ethyl]-4(R)-hydroxy-3,4,5,6-tetrahydro-2H-pyran-2-one (2h)

By following the general procedure of Example 1, Step h, but using Compound 2g in place of Compound 1g, there is obtained the desired 2h as a colorless gummy oil: nmr (CDCl3) δ 0.86 (3H, d, J=7 Hz), 2.30 (H, m), 2.63 (H, m of d, J=18 Hz), 2.76 (H of d, J=18, 5 HZ), 3.58 (H, d of d, J=11, 6 Hz), 3.81 (H, t, J=11 Hz), 4.37 (H, m), 4.60 (H, m), 5.18 (H, m).

Anal Calc'd for $C_{26}H_{42}O_6 \cdot 0.4H_2O$ C: 68.21; H: 9.42. Found C: 68.15; H: 9.53.

EXAMPLE 3
Preparation of 6(R)-[2-[8(S)-(2,2-Dimethylbutyryloxy)-6(R)-hydroxymethyl-2(S)-methyl-1,2,3,4,6,7,8,8a(R)-octahydronaphthyl-1(S)]ethyl]-4(R)-hydroxy-3,4,5,6-tetrahydro-2H-pyran-2-one

(a)
(6R)-[2-[8(S)-Hydroxy-2(S),6(R)-dimethyl-1,2,3,4,6,7,8,8a(R)-octahydronaphthyl-1(S)]ethyl]-4(R)-tert-butyldimethylsilyloxy)-3,4,5,6-tetrahydro-2H-pyran-2-one A solution (200 ml) of 50% toluene in absolute ethanol was deoxygenated by bubbling N2 through it for 15 minutes. Wilkinson's catalyst (2g) was added to the solution and the mixture reduced on the Paar hydrogenation apparatus at 50 psi H2 for 90 minutes. 6(R)-[2-[8(S)-hydroxy-2(S),6(R)-dimethyl-1,2,6,7,8,8a(R)-hexahydronaphthyl-1(S)]ethyl]-4(R)-(tert-butyldimethyl-silyloxy)-3,4,5,6-tetrahydro-2H-pyran-2-one (4.0 g, 9.0 mmol.) was added and the solution hydrogenated at 58 psi H2 for two days. The solvent was removed in vacuo and the residue stirred with diethyl ether (500 ml) for 15 minutes and then filtered. The filtrate was evaporated in vacuo to give a brown solid which was dissolved in toluene (200 ml) containing thiourea (2.6 g). The mixture was heated at 80° C. for 2 hours and then cooled to 0° C. and filtered. The filtrate was evaporated in vacuo and the solid residue chromatographed on a 7×18 cm column of silica gel. The column was eluted with 20% Ethyl acetate/hexane and 25 ml fractions were collected. Fractions 54–90 were combined and evaporated in vacuo to yield the title compound as a colorless solid; crystallization of the solid from CH3CN/H2O provided an analytical sample as colorless needles, mp 145°–6° C. nmr (CDCl3) δ 0.070 (3H, s), 0.077 (3H, s), 0.88 (9H, s), 0.90 (3H, d, J=7 Hz), 1.17 (3H, d,J=7 Hz), 2.58 (2H, m), 4.16 (H, m), 4.28 (H, m), 4.66 (H, m), 5.41 H, m).

Anal Calc'd for $C_{25}H_{44}O_4Si$: C: 68.76 H: 10.50. C: 68.72 H: 10.32.

(b)
6(R)-[2-[8(S)-(2,2-Dimethylbutyryloxy)-6(R)-hydroxymethyl-2(S)-methyl-1,2,3,4,6,7,8,8a(R)-octahydronaphthyl-1(S)]ethyl]-4(R)-hydroxy-3,4,5,6-tetrahydro-2H-pyran-2 one By substituting an equimolar amount of the title compound in Step (a) of this example for 6(R)-[2-[8(S)-hydroxy-2(S),6(S)-dimethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one in Step a of Example 1 and then following the general procedures of Steps a through h of Example 1, there is obtained a corresponding amount of the title compound as an amorphorus solid, nmr (CDCl3) δ 0.85 (3H, t, J=7 Hz), 0.90 (3H, d, J=7 Hz), 1.14 (3H, s), 1.16 (3H, s), 3.54 (H, m), 3.65 (H, m), 4.37 (H, m), 4.59 (H, m), 5.35 (H, m), 5.47 (H, m).

Anal Calc'd for $C_{25}H_{40}O_6 \cdot 0.5H_2O$: C: 67.38; H: 9.57, Found C: 67.66; H: 9.28.

EXAMPLES 4–21

Utilizing the general procedures of Examples 1 and 2 or 3 the following compounds of the formula (7) are prepared from the appropriate starting materials.

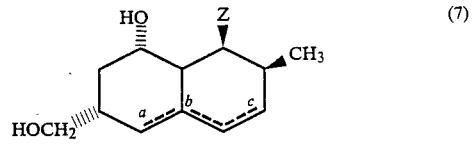

(7)

| Compound | a | b | c | X | Z |
|---|---|---|---|---|---|
| 4 | — | — | — | ![cyclohexyl-O] | XO—/=O CH2—CH2— |
| 5 | db | — | — | ![cyclohexyl-O] | XO—/=O CH2—CH2— |

| Compound | a | b | c | X | Z |
|---|---|---|---|---|---|
| 6 | — | db | — | 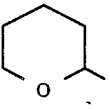 | 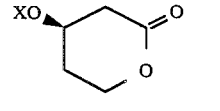 |
| 7 | — | — | db | 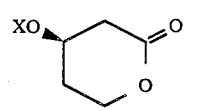 | 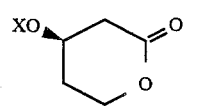 |
| 8 | — | db | — | t-butyl-dimethylsilyl | 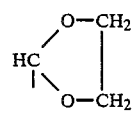 |
| 9 | — | — | db | t-butyl-dimethylsilyl | 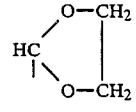 |
| 10 | — | — | — | | —CH$_2$CH$_2$CN |
| 11 | db | — | — | | —CH$_2$CH$_2$CN |
| 12 | — | db | — | | —CH$_2$CH$_2$CN |
| 13 | — | — | db | | —CH$_2$CH$_2$CN |
| 14 | — | — | — | | 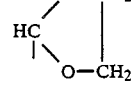 |
| 15 | db | — | — | | 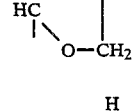 |
| 16 | — | db | — | | 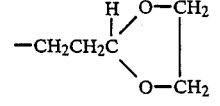 |
| 17 | — | — | db | | 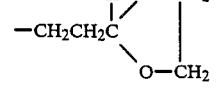 |
| 18 | — | — | — | | 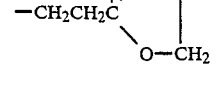 |
| 19 | db | — | — | | 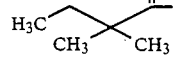 |
| 20 | — | db | — | | 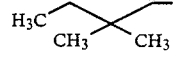 |
| 21 | — | — | db | | 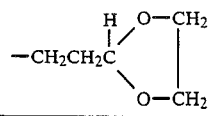 | db = double bond

EXAMPLES 22-26

Utilizing the general procedures of Examples 1 and 2 or 3 the following compounds of the formula (9) are prepared form the appropriate starting materials.

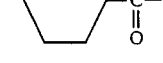

(9)

| Compounds | a | b | c | R |
|---|---|---|---|---|
| 22 | — | db | — | 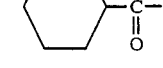 |
| 23 | — | — | db | 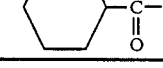 |
| 24 | db | — | — | 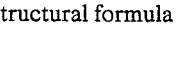 |
| 25 | — | db | — | 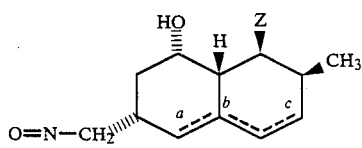 |
| 26 | — | — | db | 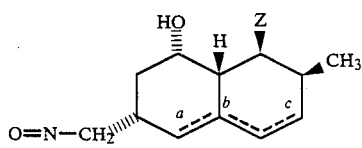 |

What is claimed is:

1. A compound represented by structural formula (3):

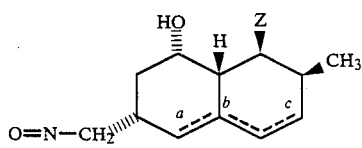

(3)

wherein a, b and c represent single bonds or one of a, b, c represents a double bond; and wherein Z is selected from a group consisting of:

a.

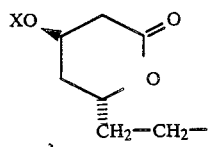

wherein X is trialkylsilyl, diarylalkylsilyl or, tetrahydropyranyl;

b.

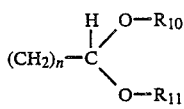

wherein n is 0 or 2 and $R_{10}$ and $R_{11}$ are independently lower alkyl or $R_{10}$ and $R_{11}$ together with the oxygens to which they are attached and the carbon bonded to the oxygens form a ring of 5 to 10 atoms.

2. A compound of claim 1 wherein Z is

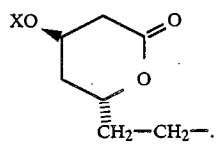

3. A compound of claim 2 wherein X is trialkylsilyl or diarylalkylsilyl.

4. A compound of claim 1 wherein a, b and c represent single bonds.

5. A compound of claim 1 wherein a represents a double bond.

6. A compound of structural formula (7)

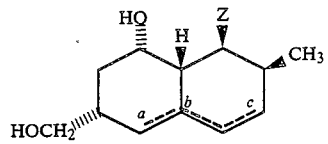

wherein a, b, c represent single bonds or one of a, b or c represents a double bond; and wherein Z is selected from a group consisting of:

a.

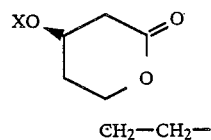

wherein X is trialkylsilyl, diarylalkylsilyl or tetrahydropyranyl;

b.

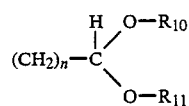

wherein n is 0 or 2 and $R_{10}$ and $R_{11}$ are independently lower alkyl or $R_{10}$ and $R_{11}$ together with the oxygens to which they are attached and the carbon bonded to the oxygens form a ring of 5 to 10 atoms.

7. A compound of claim 6 wherein Z is

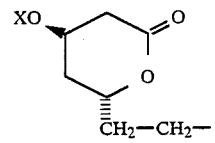

8. A compound of claim 7 wherein X is trialkylsilyl or diarylalkylsilyl.

9. A compound of claim 6 wherein a, b and c all represent single bonds.

10. A compound of claim 6 wherein a represents a double bond.

* * * * *